US00PP23522P2

(12) United States Plant Patent
Leue

(10) Patent No.: US PP23,522 P2
(45) Date of Patent: Apr. 9, 2013

(54) ***ANGELONIA* PLANT NAMED 'BALARCPUR'**

(50) Latin Name: *Angelonia angustifolia*
Varietal Denomination: Balarcpur

(75) Inventor: Ellen Leue, DeKalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 121 days.

(21) Appl. No.: 13/134,202

(22) Filed: Jun. 1, 2011

(51) Int. Cl.
*A01H 5/00* (2006.01)

(52) U.S. Cl. ..... Plt./404

(58) Field of Classification Search ..... Plt./404
See application file for complete search history.

(56) References Cited

PUBLICATIONS

Anderson. Performance of *Angelonia* Cultivars as a Summer Greenhouse Cut Flower. UK Agricultural Experimental Station, Floriculture Research Report 12-04, Jul. 2004, 1-3 pp.*

Pluto Upov Plant Variety Database 2012/04, citation for *Angelonia* AngelMist Purple, retrieved on Nov. 7, 2012. Retrieved from the Internet at <http://www.upov.int/pluto/en/index.jsp> 1 p.*

* cited by examiner

*Primary Examiner* — June Hwu
(74) *Attorney, Agent, or Firm* — Audrey Charles

(57) ABSTRACT

A new and distinct cultivar of *Angelonia* plant named 'Balarcpur', characterized by its deep lavender-blue colored flowers, dark green-colored foliage, and moderately vigorous, upright growth habit, is disclosed.

1 Drawing Sheet

Latin name of genus and species of plant claimed: *Angelonia angustifolia.*

Variety denomination: 'Balarcpur'.

BACKGROUND OF THE INVENTION

The present invention relates to a new and distinct cultivar of *Angelonia* plant botanically known as *Angelonia angustifolia* and hereinafter referred to by the cultivar name 'Balarcpur'.

The new cultivar originated in a controlled breeding program in Elburn, Ill. during November 2005. The objective of the breeding program was the development of *Angelonia* cultivars having large flowers, unique flower coloration, continuous flowering, and a moderately vigorous, freely branching, and upright to semi-upright growth habit.

The new *Angelonia* cultivar is the result of cross-pollination. The female (seed) parent of the new cultivar is the proprietary *Angelonia angustifolia* breeding selection designated 355-2, not patented, characterized by its light lavender-blue colored flowers, medium green-colored foliage, low vigor, and semi-upright growth habit. The male (pollen) parent of the new cultivar is the proprietary *Angelonia angustifolia* breeding selection designated 1549, not patented, characterized by its white-colored flowers, dark green-colored foliage, and vigorous, upright growth habit. The new cultivar was discovered and selected as a single flowering plant within the progeny of the above stated cross-pollination during December 2006 in a controlled environment in Elburn, Ill.

Asexual reproduction of the new cultivar by terminal stem cuttings since December 2006 at Elburn, Ill. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balarcpur' as a new and distinct cultivar of *Angelonia* plant:

1. Deep lavender-blue colored flowers;
2. Dark green-colored foliage; and
3. Moderately vigorous, upright growth habit.

Plants of the new cultivar differ from plants of the female parent primarily in flower color, flower size and growth habit, and from plants of the male parent primarily in flower color and flower size. Plants of the new cultivar have larger and deeper lavender-blue colored flowers than either the female or male parent.

Of the many commercially available *Angelonia* cultivars, the most similar in comparison to the new cultivar is ANGELFACE Blue Improved 'Anbluim', U.S. Pat. No. 22,390. However, in side by side comparisons, plants of the new cultivar differ from plants of 'Anbluim' in at least the following characteristics:

1. Plants of the new cultivar have more fully-opened flowers per inflorescence after 11 weeks growth than plants of 'Anbluim';
2. Plants of the new cultivar have a glabrous stem texture that is different from the densely glandular pubescent stem texture of plants of 'Anbluim'; and
3. Plants of the new cultivar are shorter than plants of 'Anbluim'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balarcpur'. The plants were grown in 4-inch pots for 11 weeks in a greenhouse at West Chicago, Ill.

DETAILED BOTANICAL DESCRIPTION

Figure 1:
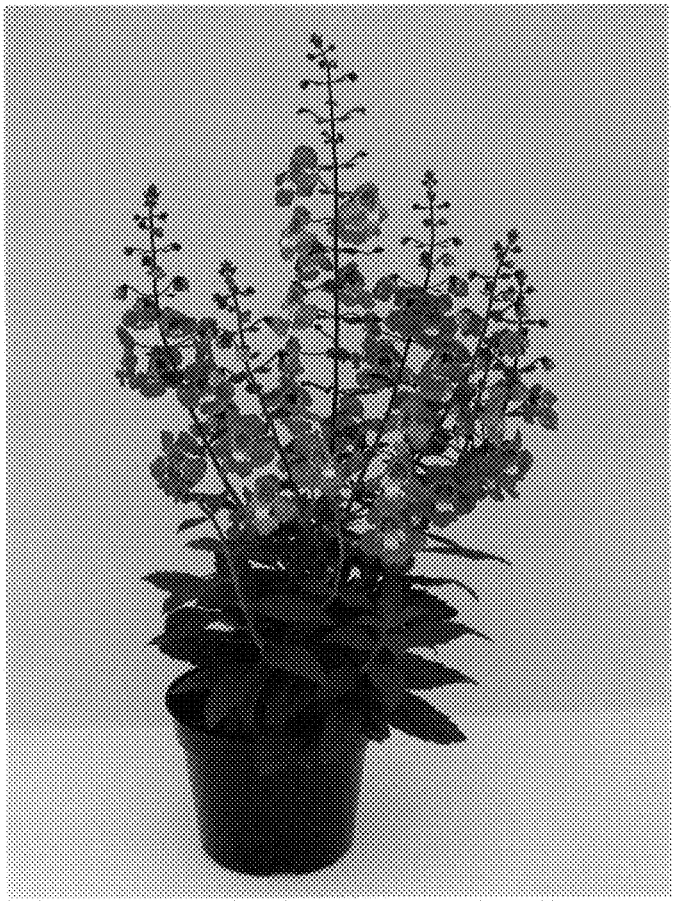
FIG. 1 illustrates a side view of the overall growth and flowering habit of 'Balarcpur'.
Figure 2:
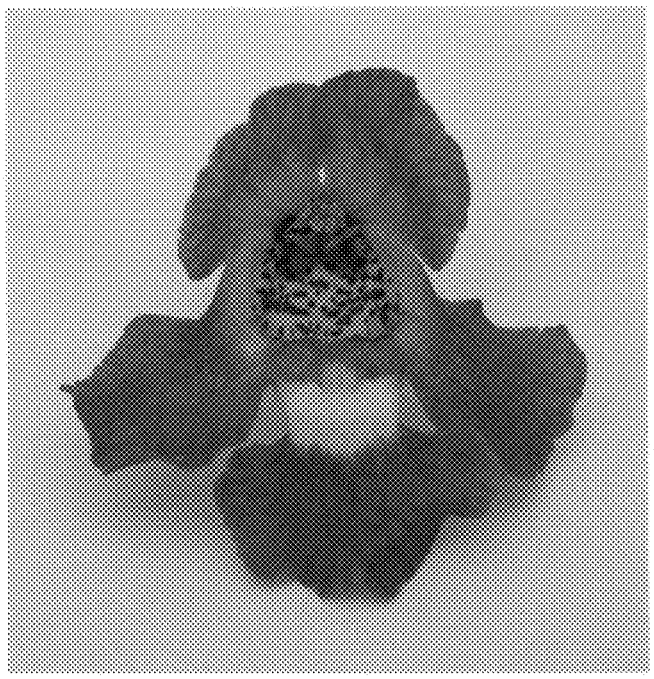
FIG. 2 illustrates a close-up view of an individual flower of 'Balarcpur'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in March 2011 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 11 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Angelonia angustifolia* cultivar Balarcpur.

Parentage:

*Female parent*.—Proprietary *Angelonia angustifolia* breeding selection designated 355-2, not patented.

*Male parent*.—Proprietary *Angelonia angustifolia* breeding selection designated 1549, not patented.

Propagation:

*Type cutting*.—Terminal stem.

*Time to initiate roots*.—Approximately 7 to 9 days.

*Time to produce a rooted cutting*.—Approximately 24 to 28 days.

*Root description*.—Fine, fibrous.

*Rooting habit*.—Freely branching.

Plant description:

*Commercial crop time*.—Approximately 5 to 8 weeks from a rooted cutting to finish in a 10 cm pot.

*Growth habit and general appearance*.—Moderately vigorous, upright.

*Size*.—Height from soil level to top of plant plane: Approximately 31.9 cm. Width: Approximately 16.8 cm.

*Branching habit*.—Freely branching. Quantity of main branches per plant: Approximately 6.

*Branch*.—Shape: Square in cross section. Strength: Moderate, somewhat brittle. Length: Approximately 20.9 cm. Diameter: Approximately 3.0 mm. Length of central internode: Approximately 1.4 cm. Texture: Glabrous. Color of young stem: 144B. Color of mature stem: 144A with an overlay of 187A.

Foliage description:

*General description*.—Quantity of leaves per main branch: Approximately 16. Fragrance: None. Form: Simple. Arrangement: Opposite.

*Leaves*.—Aspect: Perpendicular or obtuse angle to stem. Shape: Elliptic. Margin: Widely serrate. Apex: Acute. Base: Sessile. Venation pattern: Pinnate. Length of mature leaf: Approximately 7.3 cm. Width of mature leaf: Approximately 2.4 cm. Texture of upper surface: Glabrous. Texture of lower surface: Glabrous. Color of upper surface of young foliage: 137A with indistinguishable venation. Color of lower surface of young and mature foliage: N137B with midvein of 145B, other venation indistinguishable. Color of upper surface of mature foliage: Closest to 139A with indistinguishable venation.

Flowering description:

*Flowering habit*.—'Balarcpur' is freely flowering under outdoor growing conditions with substantially continuous blooming from spring through autumn and year-round in greenhouse environment.

*Lastingness of individual flower on the plant*.—Approximately 7 to 10 days.

Inflorescence description:

*General description*.—Type: Terminal raceme. Quantity per plant: Approximately 5. Fragrance: Slight, sweet. Length or height: Approximately 14.0 cm. Width: Approximately 5.5 cm. Quantity of fully open flowers per inflorescence: Approximately 7.

Flower description:

*Type*.—Solitary, zygomorphic.

*Bud*.—Rate of opening: Generally takes 3 to 4 days for bud to progress from first color to fully open flower. Quantity per inflorescence: Approximately 10.

*Bud just before opening*.—Shape: Globular. Length: Approximately 6.0 mm. Diameter: Approximately 6.0 mm. Color of upper surface: 145D and N187B. Color of lower surface: 145B.

*Corolla*.—Shape: Bilabiate. Aspect: Facing outward. Length: Approximately 3.0 cm. Width: Approximately 2.8 cm. Depth: Approximately 1.0 cm.

*Petals*.—Quantity: 5, petals are fused at base forming a throat and consisting of an upper lip with 2 petals and a lower lip with 3 petals, consisting of 2 lateral petals and one central petal. Shape: Obovate. Margin: Entire, somewhat wavy. Apex: Obtuse.

*Upper lip*.—Length of petals from throat: Approximately 9.0 mm. Width of each petal: Approximately 1.4 cm. Texture of upper surface: Sparsely glandular pubescent. Gland color: Colorless, transparent. Texture of lower surface: Glabrous. Color of upper surface when fully open: N87A. Color of lower surface when fully open: 86C.

*Lower lip, lateral petals*.—Length of petals from throat: Approximately 1.1 cm. Width of each petal: Approximately 1.3 cm. Texture of upper surface: Sparsely glandular pubescent. Texture of lower surface: Densely glandular pubescent. Gland color: Colorless, transparent. Color of upper surface when fully open: N87A. Color of lower surface when fully open: 86C.

*Lower lip, central petal*.—Length from the palate: Approximately 1.0 cm. Width: Approximately 1.4 cm. Texture of upper surface: Sparsely glandular pubescent. Texture of lower surface: Densely glandular pubescent. Gland color: Colorless, transparent. Color of upper surface when fully open: N87A. Color of lower surface when fully open: 86C.

*Throat*.—Length: Approximately 1.1 cm. Width: Approximately: 9.0 mm. Texture of inner surface: Sparsely glandular pubescent. Gland color: Mixture of colorless and 144A, transparent. Texture of outer surface: Glabrous. Color of inner surface: N87C with spots of N79A. Color of outer surface: 86D. Palate color: 144B and 155D. Palate texture: Glabrous. Teeth color: 145D.

*Calyx*.—Shape: Star, cupped. Diameter: Approximately 7.0 mm.

*Sepals*.—Quantity per flower: 5, fused at base. Shape: Lanceolate. Apex: Acute. Length: Approximately 4.0 mm. Width: Approximately 2.0 mm. Texture of upper surface: Glabrous. Texture of lower surface: Sparsely glandular pubescent. Gland color: Colorless, transparent. Color of upper surface: 139A. Color of lower surface: 139A with an overlay of N186A.

*Pedicel*.—Strength: Strong. Aspect: Acute angle to stem. Length: Approximately 1.8 cm. Diameter: Approximately 1.0 mm. Texture: Glabrous. Color: 144A with an overlay of 187A.

*Reproductive organs*.—Androecium: Stamen quantity: 4 per flower. Filament length: Approximately 4.0 mm. Filament color: N155D, opaque. Sparsely glandular pubescent. Gland color: Colorless, transparent. Anther shape: Bilobed. Anther length: Approximately 1.0 mm. Anther color: 86A. Pollen amount: Moderate. Pollen color: 155D. Gynoecium: Pistil quantity: 1 per flower. Pistil length: Approximately 5.0 mm. Stigma shape: Pointed. Stigma length: Less than 1 mm. Stigma color: Colorless, opaque. Style length: Approximately 4.0 mm. Style color: Colorless, opaque. Ovary diameter: Approximately 1.0 mm. Ovary texture: Glabrous. Ovary color: 145B.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balarcpur', substantially as herein shown and described.

* * * * *